United States Patent
Kohn et al.

(10) Patent No.: US 6,984,379 B1
(45) Date of Patent: Jan. 10, 2006

(54) GENE THERAPY BY ADMINISTRATION OF GENETICALLY ENGINEERED CD34+ CELLS OBTAINED FROM CORD BLOOD

(75) Inventors: Donald B. Kohn, Tarzana, CA (US); R. Michael Blaese, Rockville, MD (US); Craig A. Mullen, Sugar Land, TX (US); Robert C. Moen, Mountain View, CA (US)

(73) Assignees: Children's Hospital of LosAngeles, LosAngeles, CA (US); The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 08/225,478

(22) Filed: Apr. 8, 1994

(51) Int. Cl.
*A61K 48/00* (2006.01)
*C12N 15/63* (2006.01)
*C12N 15/74* (2006.01)
*C12N 15/00* (2006.01)
*C12N 5/00* (2006.01)

(52) U.S. Cl. .................... 424/93.21; 424/93.2; 514/44; 435/325; 435/320.1; 435/240.1; 435/240.2; 530/350; 536/22.1; 536/23.1; 536/24.1

(58) Field of Classification Search ............. 424/93.21, 424/93.2; 514/44; 435/320.1, 172.3, 240.1, 435/240.2, 91.1, 71.31; 530/350; 536/22.1, 536/23.1, 24.1
See application file for complete search history.

(56) References Cited

U.S. PATENT DOCUMENTS

| 5,192,553 A | 3/1993 | Boyse et al. |
| 5,399,346 A * | 3/1995 | Anderson et al. ......... 424/93.21 |
| 5,911,983 A * | 6/1999 | Barranger et al. ....... 424/93.21 |

OTHER PUBLICATIONS

Mitani et al, Philos Trans R Soc Lond B. Biol Sci, Feb. 1993, 339(1288), pp. 217-224.*
Culver et al, (Immunology section) Pediatr. Res. 31 : 149 A 1992.*
Anderson, W. F. Human Gene Therapy, Science, 256, May 8, 1992 808-813.*
Moritz et al, Human Cord Blood Cells as Targets for Gene Transfer, J. Exp. Med., vol. 178, Aug., 1993, 529-536.*
Kohn et al, Retroviral Vector Mediated Gene Transfer into Primitive Human Hemetopoietic Progenitor Cells, Exp Hematol. 20 : 1065-71 (1992).*
Marshall, Science, 269, 1995, 1050-1055.*
Uhlmann et al., Chem. Rev. 90(4): 544-588, 1990.*
Milligan et al., J. Med. Chem. 36(14): 1924-1937, 1992.*
Oakin et al., "NIH Report and Recommendations", Dec. 7, 1995 1-40.*
Kohn et al. Nat. Med. 1(10): 1017-1023, 1995.*
Culver, "Gene Therapy—A Handbook for Physicians" 1994, pp. 1-117.*
Orkin and Motulsky, 1995, "Report and Recommendationof the panel to assess the NIH investment in research on Gene therapy", NIH, Dec. 7, 1995.*
Moore, 1993, Journal of Hematotherapy, 2(2):221-224, Aug. 1993.*
Miller, et al., *Biotechniques*, vol. 7, No. 9, pp. 980-990 (1989).
Hock, et al., *Blood*, vol. 74, No. 2, pp. 876-881 (Aug. 1, 1989).
Moritz, et al., *J. Exp. Med.*, vol. 178, pp. 529-536 (Aug., 1993).

* cited by examiner

*Primary Examiner*—Anne M. Wehbe
(74) *Attorney, Agent, or Firm*—Elliot M. Olstein; Raymond J. Lillie (57) ABSTRACT

A method of providing a therapeutic effect in a human patient which comprises administering to the patient CD34+ cells obtained from cord blood. The CD34+ cells have been engineered with at least one nucleic acid sequence encoding a therapeutic agent. Such CD34+ cells may be engineered by transducing the cells with a retroviral vector including the nucleic acid sequence encoding the therapeutic agent. This method has been applied in treating newborn infants suffering from ADA deficiency.

16 Claims, 6 Drawing Sheets

FIG. 1

SEQUENCE OF THE MULTIPLE CLONING SITE IN THE pGI PLASMID

| 1/2 EcoRI | Not I | SnaBI | SalI | BamHI | XhoI | HindIII | ApaI |
|---|---|---|---|---|---|---|---|
| AATTC | GCGGCCGC | TACGTA | GTCGAC | GGATCC | CTCGAG | AAGCTT | GGGCCC |
| G | CGCCGGCG | ATGCAT | CAGCTG | CCTAGG | GAGCTC | TTCGAA | CCCGGG |

| 1/2 ClaI |
|---|
| AT |
| TAGC |

GENE THERAPY BY ADMINISTRATION OF GENETICALLY ENGINEERED CD34+ CELLS OBTAINED FROM CORD BLOOD

This invention relates to gene therapy. More particularly, this invention relates to gene therapy in a human patient by administering to the patient CD34+ cells genetically engineered with at least one DNA sequence encoding a therapeutic agent.

BACKGROUND OF THE INVENTION

Human umbilical cord blood (UCB) can be a source of hematopoietic stem cells for gene therapy, as an alternative to allogenic bone-marrow transplantation, for the treatment of a number of genetic diseases.

Previous work has examined conditions for optimal retroviral mediated gene transduction of human bone marrow progenitor cells. It has been found that pre-stimulation of marrow (either the total mononuclear cell fraction or isolated CD34+ cells) with combinations of hematopoietic growth factors increases the extent of gene transfer. For example, IL-3 and IL-6 increased gene transfer from 10% to 50%. (Nolta, et al., *Human Gene Therapy*, Vol. 1, pgs. 257–268 (1990)). Addition of c-kit ligand provided a further increase in gene transfer efficiency. (Nolta, et al., *Exp. Hematol.*, Vol. 20, pgs. 1065–1071 (1992)). The cytokines may act, at least in part, by inducing cell cycling which is required for retroviral integration. (Nolta, et al., 1990.)

The above studies were performed using the method of co-cultivation, in which the bone marrow cells are grown upon a monolayer of vector-producing fibroblasts. Initial attempts to obtain efficient gene transfer into human marrow progenitor cells using cell-free retroviral supernatants consistently yielded lower levels of gene transfer than can be achieved by using co-cultivation. Moore, et al., *Blood*, Vol. 79, pgs. 1393–1399 (1992) reported that the presence of an underlayer of marrow stromal cells facilitates efficient cell-free retroviral transduction of human marrow progenitor cells, which eliminated the need for co-culture on the murine vector packaging cells.

Umbilical cord and placental blood represent a uniquely rich source of hematopoietic stem cells. (Broxmeyer, et al., *Proc. Nat. Acad. Sci.*, Vol. 86, pg. 3828 (1989)). Large numbers of stem cells can be collected from normal cord and placental blood without cytokine mobilization and without performing invasive procedures on the patient. Based on quantitative progenitor assays it has been estimated that there are a sufficient number of progenitors in a single cord/placental blood collection to reconstitute an adult after marrow ablation. (Broxmeyer, et al., *Proc. Nat. Acad. Sci.*, Vol. 89, pg. 4109 (1992)). Within two days of birth, the number of circulating hematopoietic progenitor cells drops dramatically to the level seen in older children and adults; thus, collection of stem cells at birth from the cord or placenta represents a unique opportunity to obtain cells needed for gene therapy (such as, for example, gene therapy for ADA deficiency) easily and safely. Successful reconstitution of more than 50 children with hemoglobinopathies and with malignancies by allogenic cord blood has been performed. (Broxmeyer, et al., *Blood Cells*, Vol. 17, pg. 313 (1991); McGlave, *Blood Cells*, Vol. 17, pg. 330 (1991); Gluckman, et al., *N. Engl. J. Med.*, Vol. 321, pg. 1174 (1989); Flomenberg, et al., *Bone Marrow Transplant*, Vol. 10, Suppl. 1, pg. 115 (1992)).

Some conditions which permit in vitro gene transfer into umbilical cord blood cells recently have been described. Moritz, et al., *J. Exp. Med.*, Vol. 178, pgs. 529–536 (August 1993) found that co-cultivation of the cells was most efficient, viral supernatant transduction on a marrow stromal layer was almost as effective, and transduction with viral supernatant alone was less effective. These experiments also involved the use of c-kit ligand and Interleukin-6 in the culture medium.

DETAILED DESCRIPTION OF THE INVENTION

It is an object of the present invention to provide a method of providing for optimal transduction of CD34+ cells obtained from cord blood, and to administer such cells in a gene therapy treatment.

In accordance with an aspect of the present invention, there is provided a method of providing a therapeutic effect in a human patient. The method comprises administering to the patient CD34+ cells obtained from cord blood. The CD34+ cells have been genetically engineered to include least one nucleic acid sequence encoding a therapeutic agent.

The term "nucleic acid sequence" as used herein, means a DNA or RNA molecule, and includes complete and partial gene sequences, and includes polynucleotides as well. Such term also includes a linear series of deoxyribonucleotides or ribonucleotides connected one to the other by phosphodiester bonds between the 3' and 5' carbons of the adjacent pentoses.

The at least one nucleic acid sequence is contained in at least one expression vehicle. The term "expression vehicle" as used herein means any genetic construct including the at least one nucleic acid sequence, and is capable of providing for expression of such sequence.

The expression vehicle may be any expression vehicle which is capable of transfecting cells and expressing the at least one nucleic acid sequence in vivo. Such expression vehicles include, but are not limited to, eukaryotic vectors, prokaryotic vectors (such as, for example, bacterial plasmids), and viral vectors. The expression vehicle also may be contained within a liposome.

In one embodiment, the expression vehicle is a viral vector. Viral vectors which may be employed include, but are not limited to, retroviral vectors, adenovirus vectors, adeno-associated virus vectors, and Herpes Virus vectors. Preferably, the viral vector is a retroviral vector.

In a preferred embodiment, a packaging cell line is transduced with the viral vector, which includes the at least one nucleic acid sequence which encodes a therapeutic agent, to form a producer cell line including the viral vector. The producer cell line generates viral particles capable of transducing the CD34+ cells obtained from cord blood.

In a preferred embodiment, the viral vector is a retroviral vector. Examples of retroviral vectors which may be employed include, but are not limited to, Moloney Murine Leukemia Virus, spleen necrosis virus, and vectors derived from retroviruses such as Rous Sarcoma Virus, Harvey Sarcoma Virus, avian leukosis virus, gibbon ape leukemia virus, human immunodeficiency virus, myeloproliferative sarcoma virus, and mammary tumor virus. Preferably, the retroviral vector is an infectious but non-replication competent retrovirus; however, replication competent retroviruses may also be used.

Retroviral vectors are useful as agents to mediate retroviral-mediated gene transfer into eukaryotic cells. Retroviral vectors generally are constructed such that the majority of sequences coding for the structural genes of the virus are deleted and replaced by the gene(s) of interest. Most often, the structural genes (i.e., gag, pol, and env), are removed from the retroviral backbone using genetic engineering techniques known in the art. This may include digestion with the appropriate restriction endonuclease or, in some instances, with Bal 31 exonuclease to generate fragments containing appropriate portions of the packaging signal.

These new genes have been incorporated into the proviral backbone in several general ways. The most straightforward constructions are ones in which the structural genes of the retrovirus are replaced by a single gene which then is transcribed under the control of the viral regulatory sequences within the long terminal repeat (LTR). Retroviral vectors have also been constructed which can introduce more than one gene into target cells. Usually, in such vectors one gene is under the regulatory control of the viral LTR, while the second gene is expressed either off a spliced message or is under the regulation of its own, internal promoter.

Efforts have been directed at minimizing the viral component of the viral backbone, largely in an effort to reduce the chance for recombination between the vector and the packaging-defective helper virus within packaging cells. A packaging-defective helper virus is necessary to provide the structural genes of a retrovirus, which have been deleted from the vector itself.

In one embodiment, the retroviral vector may be one of a series of vectors described in Bender, et al., *J. Virol.* 61:1639–1649 (1987), based on the N2 vector (Armentano, et al., *J. Virol.*, 61:1647–1650) containing a series of deletions and substitutions to reduce to an absolute minimum the homology between the vector and packaging systems. These changes have also reduced the likelihood that viral proteins would be expressed. In the first of these vectors, LNL-XHC, there was altered, by site-directed mutagenesis, the natural ATG start codon of gag to TAG, thereby eliminating unintended protein synthesis from that point. In Moloney murine leukemia virus (MoMuLV), 5' to the authentic gag start, an open reading frame exists which permits expression of another glycosylated protein (pPr80$^{gag}$). Moloney murine sarcoma virus (MoMuSV) has alterations in this 5' region, including a frameshift and loss of glycosylation sites, which obviate potential expression of the amino terminus of pPr80$^{gag}$. Therefore, the vector LNL6 was made, which incorporated both the altered ATG of LNL-XHC and the 5' portion of MoMuSV. The 5' structure of the LN vector series thus eliminates the possibility of expression of retroviral reading frames, with the subsequent production of viral antigens in genetically transduced target cells. In a final alteration to reduce overlap with packaging-defective helper virus, Miller has eliminated extra env sequences immediately preceding the 3' LTR in the LN vector (Miller, et al., *Biotechniques,* 7:980–990, 1989).

The paramount need that must be satisfied by any gene transfer system for its application to gene therapy is safety. Safety is derived from the combination of vector genome structure together with the packaging system that is utilized for production of the infectious vector. Miller, et al. have developed the combination of the pPAM3 plasmid (the packaging-defective helper genome) for expression of retroviral structural proteins together with the LN vector series to make a vector packaging system where the generation of recombinant wild-type retrovirus is reduced to a minimum through the elimination of nearly all sites of recombination between the vector genome and the packaging-defective helper genome (i.e. LN with pPAM3).

In one embodiment, the retroviral vector may be a Moloney Murine Leukemia Virus of the LN series of vectors, such as those hereinabove mentioned, and described further in Bender, et al. (1987) and Miller, et al. (1989). Such vectors have a portion of the packaging signal derived from a mouse sarcoma virus, and a mutated gag initiation codon. The term "mutated" as used herein means that the gag initiation codon has been deleted or altered such that the gag protein or fragments or truncations thereof, are not expressed.

In another embodiment, the retroviral vector may include at least four cloning, or restriction enzyme recognition sites, wherein at least two of the sites have an average frequency of appearance in eukaryotic genes of less than once in 10,000 base pairs; i.e., the restriction product has an average DNA size of at least 10,000 base pairs. Preferred cloning sites are selected from the group consisting of NotI, SnaBI, SalI, and XhoI. In a preferred embodiment, the retroviral vector includes each of these cloning sites. Such vectors are further described in U.S. patent application Ser. No. 919, 062, filed Jul. 23, 1992, and incorporated herein by reference in its entirety.

When a retroviral vector including such cloning sites is employed, there may also be provided a shuttle cloning vector which includes at least two cloning sites which are compatible with at least two cloning sites selected from the group consisting of NotI, SnaBI, SalI, and XhoI located on the retroviral vector. The shuttle cloning vector also includes at least one desired gene which is capable of being transferred from the shuttle cloning vector to the retroviral vector.

The shuttle cloning vector may be constructed from a basic "backbone" vector or fragment to which are ligated one or more linkers which include cloning or restriction enzyme recognition sites. Included in the cloning sites are the compatible, or complementary cloning sites hereinabove described. Genes and/or promoters having ends corresponding to the restriction sites of the shuttle vector may be ligated into the shuttle vector through techniques known in the art.

The shuttle cloning vector can be employed to amplify DNA sequences in prokaryotic systems. The shuttle cloning vector may be prepared from plasmids generally used in prokaryotic systems and in particular in bacteria. Thus, for example, the shuttle cloning vector may be derived from plasmids such as pBR322; pUC 18; etc.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, TK promoters, and B19 parvovirus promoters. The selection of a suitable promoter will be apparent to those skilled in the art from the teachings contained herein.

The vector then is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and CaPO$_4$ precipitation.

The producer cell line generates infectious but non-replicating viral vector particles which-include the at least one therapeutic agent. Such vector particles then may be employed to transduce CD34+ cells, which will express the nucleic acid sequence encoding the therapeutic agent. The vector particles may transduce the CD34+ cells at a multiplicity of infection of from 1 to 20 vectors per cell, preferably from 2 to 10 vectors per cell, and more preferably at about 6 vectors per cell.

The CD34+ cells are obtained from cord blood by any of a variety of accepted means known to those skilled in the art. For example, umbilical cord blood may be obtained from a normal term delivery by gravity drainage from the umbilical cord stump into an anticoagulant. The mononuclear cells, in one embodiment, may be isolated by centrifugation on a two-step Ficoll/Hypaque 72% Percoll gradient, and by collecting and pooling the cells at both the plasma/Ficoll and Ficoll/Percoll interfaces.

Various techniques for isolating and storing cord blood and obtaining stem and progenitor cells from such blood are disclosed in U.S. Pat. No. 5,192,533, issued Mar. 9, 1993, to Boyse, et al.

In one embodiment, CD34+ cells are isolated using the Cell Pro CEPRATE system. (Berenson, et al., *Blood*, Vol. 77, pg. 1717 (1991); Berenson, et al., *J. Clin. Invest.*, Vol. 81, pg. 951 (1988)). In such embodiment, CD34+ cells may be isolated from cord blood by an immunoabsorption technique that utilizes anti-CD 34 antibody 12.8 and a solid phase avidin-biotin column. (Berenson, et al., *Blood*, Vol. 77, pg. 1717 (1991); Berenson, et al., *J. Clin. Invest.*, Vol. 81, pg. 951 (1988)). Final purities, as assessed by FACS, may be from 50% to 90%, and 50- to 150-fold enrichment of CD34+ cells may be obtained. (Heimfeld, et al., *Blood*, Vol. 78, Suppl. 1, pg. 16a (1991); Berenson, 1991; Bensinger, et al., *Prog. Clin. Biol. Res.*, Vol. 337, pg. 93 (1990)).

The CD34+ cells in one embodiment may be co-cultured with the producer cells. In another embodiment, the CD34+ cells are cultured during transduction on a layer of bone marrow stromal cells. In yet another embodiment, the CD34+ cells, during transduction, are cultured in the presence of at least one cytokine. Cytokines which may be added to the culture of CD34+ cells during the transduction of such cells include, but are not limited to, Interleukin-1α, Interleukin-3, Interleukin-6, Interleukin-11, Interleukin-12, Flt-3 ligand, leukemia inhibitory factor (LIF), and c-kit ligand, also known as mast cell growth factor, or MGF, or stem cell factor. In a preferred embodiment, the CD34+ cells are cultured in the presence of Interleukin-3, Interleukin-6, and MGF or stem cell factor. Applicants have found that, by culturing the CD34+ cells in the presence of Interleukin-3, Interleukin-6, and c-kit ligand, one achieves improved transduction of the CD34+ cells with the infectious retroviral vector particles.

The transduced CD34+ cells then may be administered to a human patient in an amount effective to produce a therapeutic effect in the patient. In general, such cells are administered in an amount of from about $5 \times 10^5$/kg to about $10 \times 10^7$/kg, preferably from about $5 \times 10^5$/kg to about $1 \times 10^7$/kg, and more preferably from about $5 \times 10^5$/kg. to about $5 \times 10^6$/kg. The number of cells administered is dependent upon a variety of factors, including, but not limited to, the age, sex, and weight of the patient, the disease to be treated, and the severity thereof.

The term "therapeutic" is used in a generic sense and includes treating agents, prophylactic agents, and replacement agents.

Nucleic acid sequences encoding therapeutic agents which may be placed into the vector include, but are not limited to, nucleic acid sequences encoding cytokines, tumor necrosis factor (TNF) genes, such as TNF-α; genes encoding interferons such as Interferon-α, Interferon-β, and Interferon-γ; genes encoding interleukins such as Il-1, IL-1β, and Interleukins 2 through 14; the gamma chain of the IL-2 receptor; genes encoding GM-CSF; genes encoding adenosine deaminase, or ADA; genes which encode cellular growth factors, such as lymphokines, which are growth factors for lymphocytes; genes encoding soluble CD4; Factor VIII; Factor IX; T-cell receptors; the LDL receptor, ApoE, ApoC, ApoAI and other genes involved in cholesterol transport and metabolism; the alpha-1 antitrypsin (α1AT) gene, the ornithine transcarbamylase (OTC) gene, the CFTR gene, the insulin gene, viral thymidine kinase genes, such as the Herpes Simplex Virus thymidine kinase gene, the cytomegalovirus virus thymidine kinase gene, and the varicella-zoster virus thymidine kinase gene; ZAP70 transcription factor; Fc receptors for antigen-binding domains of antibodies, the RAG1 and RAG2 genes, which encode enzymes that are essential for assembly of T-cell and B-cell receptors, and antisense sequences such as those that inhibit viral replication, such as antisense sequences which inhibit replication of hepatitis B or hepatitis non-A non-B virus.

The promoters which control such genes may be those as hereinabove described, or such genes may be controlled by their own native promoters.

It is to be understood, however, that the scope of the present invention is not to be limited to specific foreign genes or promoters.

The method of the present invention is particularly applicable to the treatment of newborn infants who have been determined to have severe combined immune deficiency (SCID) caused by, for example, adenosine deaminase (ADA) deficiency. Thus, in one embodiment, umbilical cord blood is obtained from the umbilical cord stump of a newborn infant determined to have severe combined immune deficiency. The CD34+ cells then are separated from the cord blood by methods such as those hereinabove described. The CD34+ cells then are cultured in a medium which also includes Interleukin-3, Interleukin-6, and stem cell factor. The cells then are transduced with retroviral vector particles which include a nucleic acid sequence encoding the adenosine deaminase (ADA) gene. After the transduced cells are cultured, they are administered to the infant intravenously in an effective therapeutic amount.

BRIEF DESCRIPTION OF THE DRAWINGS

The invention will now be described with respect to the drawings, wherein.

EXAMPLES

The invention will now be described with respect to the following examples; however, the scope of the present invention is not intended to be limited thereby.

Example 1

A. Construction of pG1NaSvAd

Figure 1:
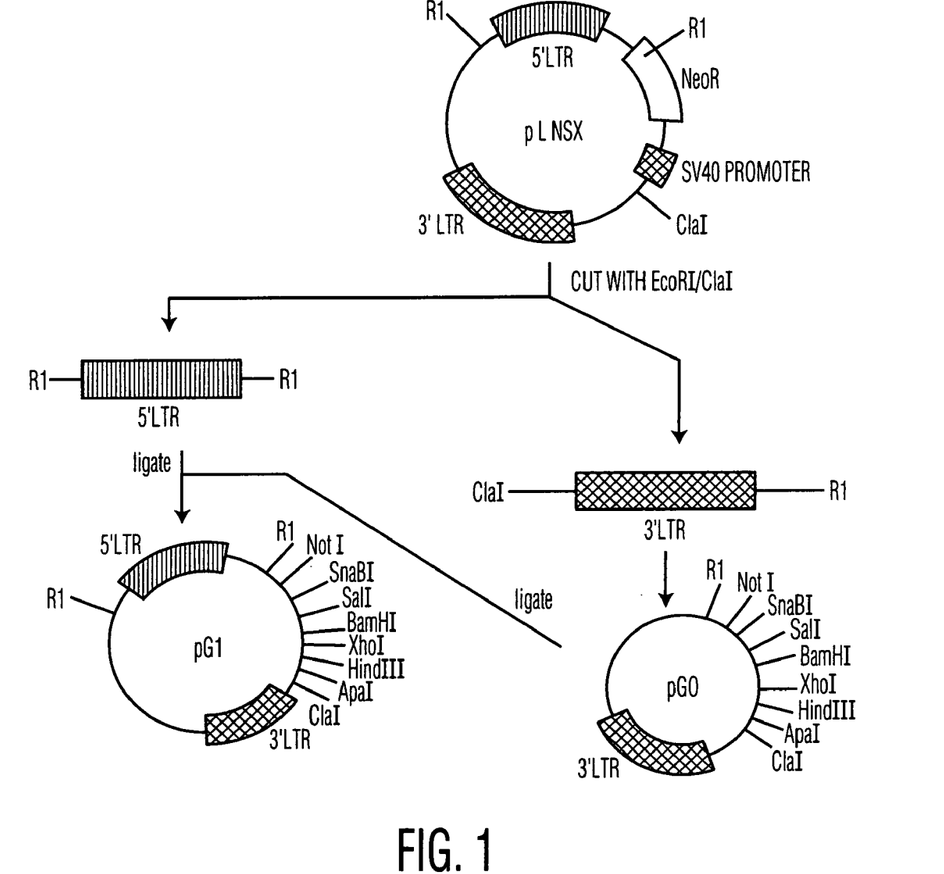
FIG. 1 is a schematic of the construction of plasmid pG1.
Figure 2:
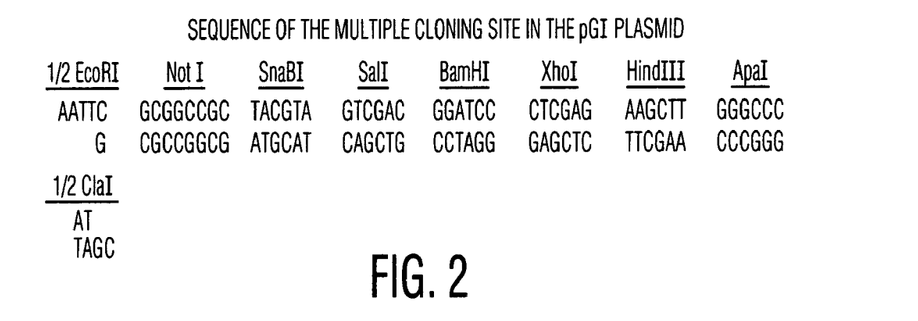
FIG. 2 is the sequence of the multiple cloning site in plasmid pG1 (SEQ ID NO:1)
Figure 3:
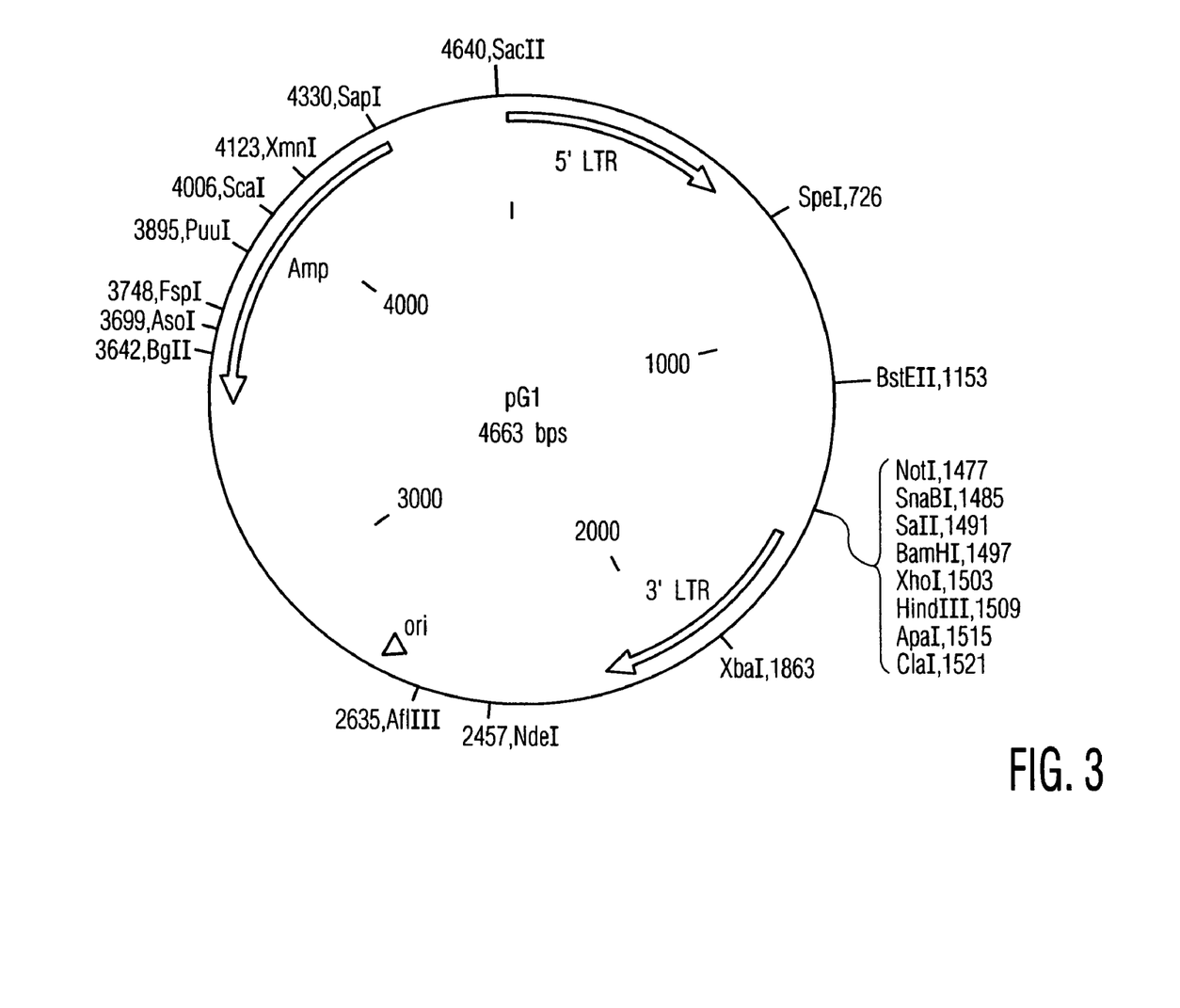
FIG. 3 is a map of plasmid pG1.

Plasmid pG1NaSvAd was constructed from the backbone of plasmid pG1. Plasmid pG1 was constructed from PLNSX (Palmer et al., *Blood*, 73:438–445; 1989). The construction strategy for plasmid pG1 is shown in FIG. 1. The 1.6 kb EcoRI fragment, containing the 5' Moloney Sarcoma Virus (MoMuSV) LTR, and the 3.0 kb EcoRI/ClaI fragment, containing the 3' LTR, the bacterial origin of replication and the ampicillin resistance gene, were isolated separately. A linker containing seven unique cloning sites was then used to close the EcoRI/ClaI fragment on itself, thus generating the plasmid pGO. The plasmid pGO was used to generate the vector plasmid pG1 by the insertion of the 1.6 kb EcoRI fragment containing the 5' LTR into the unique EcoRI site of pGO. Thus, pG1(FIG. 3) consists of a retroviral vector backbone composed of a 5' portion derived from MoMuSV, a short portion of gag in which the authentic ATG start codon has been mutated to TAG (Bender et al. 1987), a 54 base pair multiple cloning site (MCS) containing from 5' to 3' the sites EcoRI, NotI, SnaBI, SalI, BamHI, XhoI, HindIII, ApaI, and ClaI, and a 3' portion of MoMuLV from base pairs 7764 to 7813 numbered as described in (Van Beveren et al., *Cold Spring Harbor*, Vol. 2, pg. 567, 1985). (FIG. 2). The MCS was designed to generate a maximum number of unique insertion sites, based on a screen of non-cutting restriction enzymes of the pG1 plasmid, the $neo^R$ gene, the β-galactosidase gene, the $hygromycin^R$ gene, and the SV40 promoter.

Figure 4:
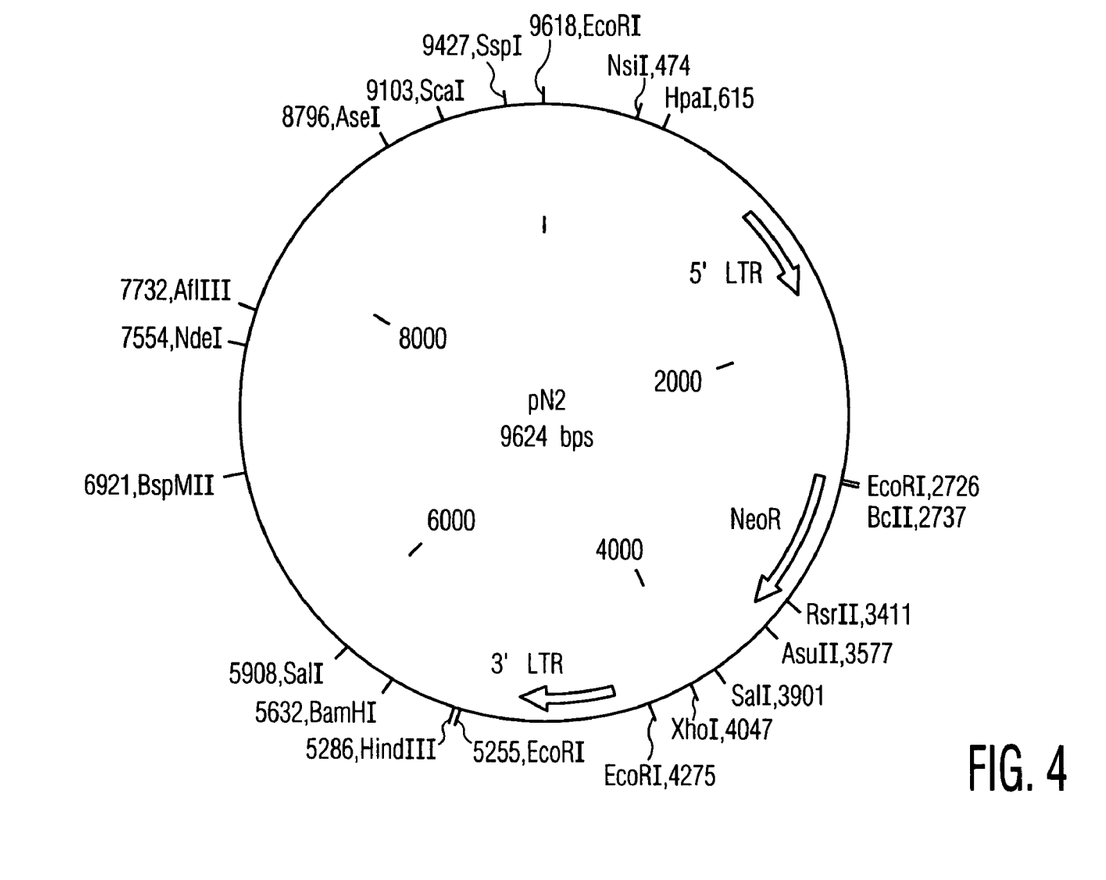
FIG. 4 is a map of plasmid pN2.
Figure 5:
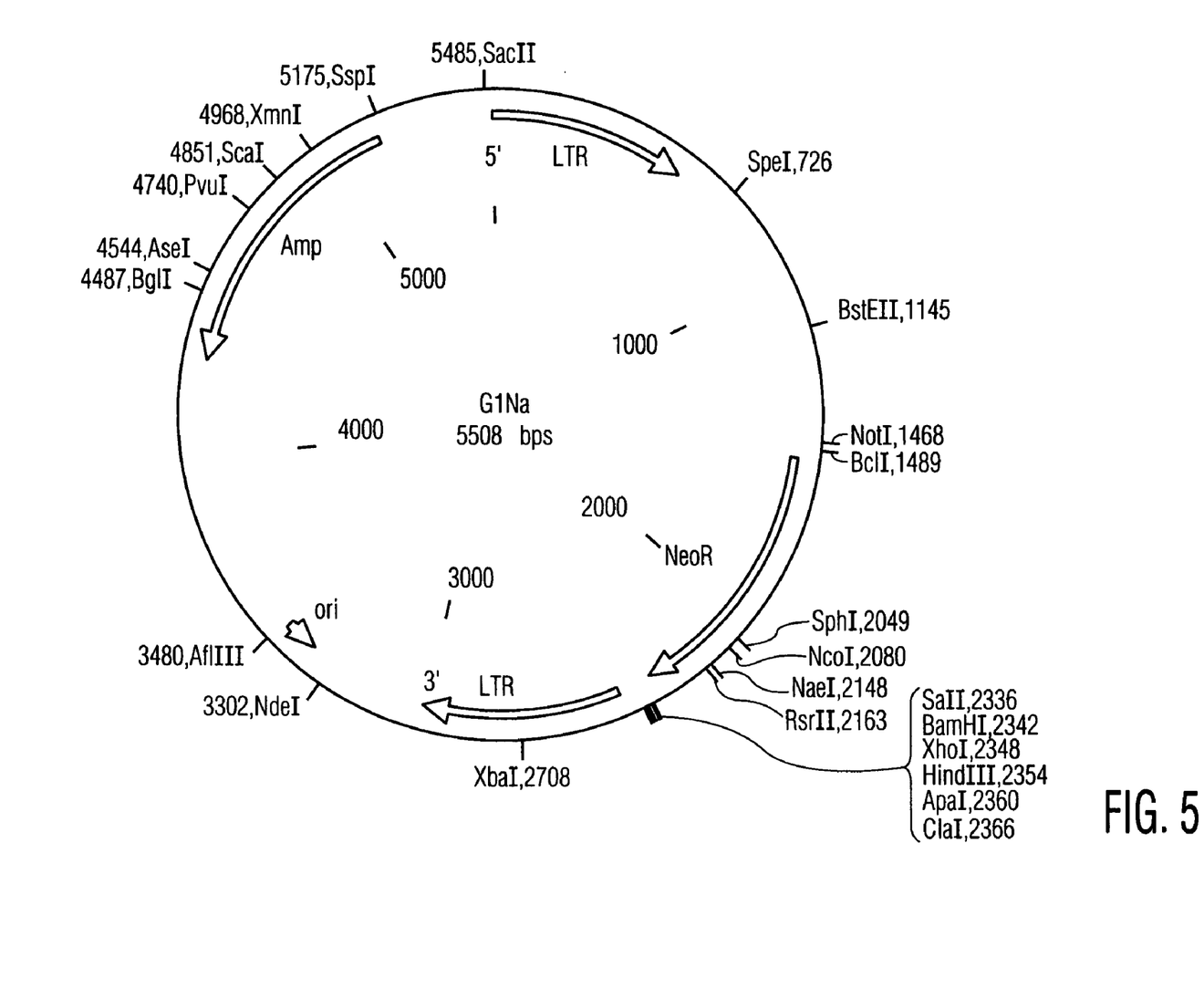
FIG. 5 is a map of plasmid pG1Na.
Figure 6:
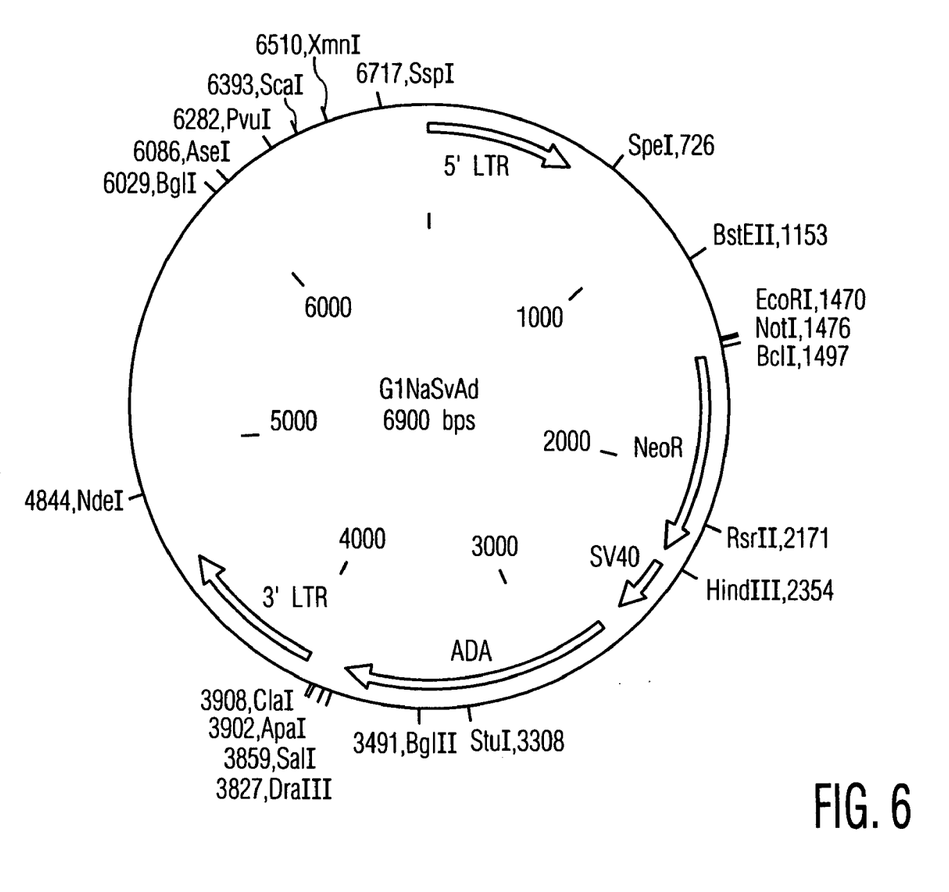
FIG. 6 is a map of plasmid pG1NaSvADA.

The "backbone" vector pG1Na was constructed from pG1 and pN2 (Armentano, et-al., *J. Virology*, Vol. 61, pgs. 1647–1650 (1987)). pG1Na was constructed by cutting pN2 (FIG. 4) with EcoRI and AsuII, filling in the ends of the EcoRI/AsuII fragment containing the $neo^R$ gene, and ligating the fragment into SnaBI digested pG1 to form pG1Na (FIG. 5).

pG1Na was cut with Hind III and SalI, and the ends were filled in with Klenow. A fragment containing human ADA cDNA (ATCC Accession Nos. 57226, 77670 and 78563) under the control of an SV40 promoter is ligated to the end-filled HindIII/SalI digested pG1Na to form pG1NaSvAd. (FIG. 6).

B. Generation of Producer Cell Line

A producer cell line was made from vector plasmid and packaging cells. The PA317/G1NaSvAd producer cell was made by the same general techniques used to make previous clinically relevant retroviral vector producer cell lines. The vector plasmid pG1NaSvAd DNA was transfected into a ecotropic packaging cell line, PE501. Supernatant from the PE501 transfected cells was then used to transinfect the amphotropic, hTK containing, packaging cell line (PA317). Clones of transinfected producer cells were then grown in G418 containing medium to select clones that contain the $Neo^R$ gene. The clones were then titered for retroviral vector production. Several clones were then selected for further testing and finally a clone was selected for clinical use.

$5 \times 10^5$ PE501 cells (Miller, et al., *Biotechniques*, Vol. 7, pgs. 980–990 (1989), incorporated herein by reference) were plated in 100 mm dishes with 10 ml high glucose Dulbecco's Modified Essential Medium (DMEM) growth medium supplemented with 10% fetal bovine serum (HGD10) per dish (3–100 mm dishes are required per transfection). The cells were incubated at 37° C., in a 5% $CO_2$ atmosphere overnight.

The plasmid pG1NaSvAd then was transfected into PE501 cells by $CaPO_4$ precipitation using 50 μg of DNA by the following procedure.

50 μg of DNA, 50 μl 10×$CaCl_2$, and 450 μl of sterile $H_2O$ was mixed in a 15 ml polypropylene tube to yield a 0.25M $CaCl_2$ solution containing 50 μg DNA, 0.5 ml 2× BBS (containing 50 mM N-N-bis-( 2-hydroxyethyl)-2-aminoethane-sulfonic acid, 280 mM Na Cl, 1.5 mM$Na_2$ $HPO_4$, and 50 mM Hepes, pH6.95), then was added to the tube and the contents of the tube were mixed by pipetting. The DNA solution then was left at room temperature for about 20 minutes to 1 hour. 1 ml of DNA solution then was added to each culture dish, and each dish was swirled to ensure even distribution of the DNA. The dishes then were incubated at 35° C. in a 3% $CO_2$ atmosphere overnight.

A culture dish(es) with optimum precipitate following the overnight incubation then was selected. The medium/DNA precipitate was aspirated from the dish(es), and 5 mL PBS was added to each dish. The dish(es) was allowed to sit for 2 to 3 minutes to allow salts to dissolve.

The dish(es) then was washed again with PBS to remove the salt and the salt solution. 10 ml of HGD10 medium then was added to the dish(es), and the dish(es) incubated at 37° C. in a 5% $CO_2$ atmosphere for about 48 hrs.

A 48 hour transient supernatant then was collected from the transfected cells by removing the supernatant from the cells and placing it in a 15 ml polypropylene tube. The dish(es) then was rinsed with 5 ml PBS. The PBS then was removed, and 1 ml trypsin-EDTA was added to each dish. Three 15 ml polypropylene tubes then were labeled undiluted, 1:10, and 1:100, respectively. 9 ml of HGD10 plus 0.8 mg/ml of G418 were added to the 1:10 and the 1:100 tubes.

When the cells were no longer adherent to the dish, 9 ml of HGD10 and 0.8 mg/ml of G418 were added to the undiluted tube, and the cells transferred to the undiluted tube.

Serial dilutions of the cells then were made by adding 1 ml of undiluted cells to the 1:10 tube, and then by adding 1 ml of the 1:10 cells to the 1:100 tube. The cells then were mixed.

10 ml of HGD10 and 0.8 mg/ml G418 were added to each of six 100 mm dishes. To one dish was added 0.5 ml of undiluted cells to make a 1:20 dilution of cells; to one dish was added 0.25 ml of undiluted cells to make a 1:40 dilution of cells; to one dish was added 1.0 ml of the 1:10 dilution to make a 1:100 dilution of cells; to one dish was added 0.2 ml of the 1:10 dilution to make a 1:500 dilution of cells; to one dish was added 1.0 ml of the 1:100 dilution to make a 1:1,000 dilution of cells; and to another dish was added 0.5 ml of the 1:100 dilution to make a 1:2,000 dilution of cells.

The six plates of cells were examined daily. The medium was changed if there was a great amount of cell death. Such medium changes were repeated until few dead cells were observed. At this point, live cells or colonies were allowed to grow to a size such that the colonies are large enough to clone out (i.e., the colonies are visible to the naked eye when looking up through the bottom of the plate). Viral supernatants from such colonies of PE501 cells were collected in amounts of from about 5 ml to about 10 ml, placed in cryotubes, and frozen in liquid nitrogen at about −70° C.

PA317 cells (Miller et al., *Mol. Cell. Biol.*, 6:2895–2902 (1986) and incorporated herein by reference) then were plated at a density of 5×10⁴ cells per 100 mm plate on Dulbecco's Modified Essential Medium (DMEM) including 4.5 g/l glucose, glutamine supplement, and 10% fetal bovine serum (FBS).

The viral supernatant then was thawed, and 8 μg/ml of polybrene was added to viral supernatant from PE 501 cells, and the supernatant and polybrene were mixed and loaded into a syringe with a 0.22 μm filter unit. The DMEM was suctioned off the plate of cells, and 7 to 8 ml of viral supernatant was added for overnight infection.

The viral supernatant then was removed and replaced with fresh 10% FBS. One day later, the medium was changed to 10% FBS and G418 (800 μg/ml). The plate then was monitored, and the medium was changed to fresh 10% FBS and G418 to eliminate dying or dead cells whenever necessary. The plate also was monitored for at least 10 to 14 days for the appearance of G418 resistant colonies by scanning the bottom of the dish without a microscope. When colonies are large enough to see, they then were selected as clones.

The medium then was aspirated from the dish and replaced with 5 ml PBS. The cells then were rinsed and most of the PBS was aspirated. About 0.5 to 1.0 ml of the PBS was left on the plate to keep it moist. Cloning rings then are placed on all selected colonies. Two drops of trypsin-EDTA then were placed on each cloning ring. The dish then was placed in an incubator, and tapped periodically until the cells are released from the dish. 5 ml of HGD10 plus 1× hypoxanthine aminopterin thymidine (HAT) was added to as many wells as needed in six well dishes.

When the cells from each colony were released from the dish, 2 drops of HGD10 are added to each cloning ring. A pipette then was set to 200 μl, and inserted into a cloning ring in order to remove all the cells. The cells then were transferred to one of the wells in the 6-well dishes. Such procedure was repeated until all desired clones were picked. The 6-well dishes were incubated at 37° C. in a 5% $CO_2$ atmosphere.

The clones then were observed for confluent growth. When a clone was confluent or almost confluent, the clone was trypsinized and expanded in a 100 ml dish.

When the expanded clone was about 90% confluent, the old medium was removed and replaced with 10 ml of fresh HGD10 medium. The dish was returned to the incubator for 20 to 24 hours.

After the incubation, the supernatant was removed from the dish, and placed in a 15 ml polypropylene tube. The tube was centrifuged at 1,200 to 1,500 rpm for 5 minutes to pellet out any cells which may have been in the supernatant.

The supernatant then was aliquoted into six cryovials (1 ml/vial). The aliquots were stored in liquid nitrogen. 5 ml of PBS were added to the dish and the cells were rinsed.

When the cells were released from the dish, 9 ml of HGD10 was added to the cells, and the cells were transferred to a 15 ml polypropylene tube. The cells were pelleted by centrifuging at 1,200–1,500 rpm for 5 minutes.

The medium was aspirated off the cell pellet. The pellet then was resuspended in 1 ml HGD 10 and 1 ml of 2×DMSO freezing medium, and 1 ml of cells was aliquoted into each of two cryovials. The cryovials were placed on dry ice, and, when frozen, were transferred to liquid nitrogen.

Through the above procedures, the producer cell line PA317/G1NaSvAd, was obtained. This cell line produces the viral vector G1NaSvAd at a titer of 2–5×10⁵ cfu/ml.

C. Generation of Producer Cell Line From LN Vector

Figure 7:
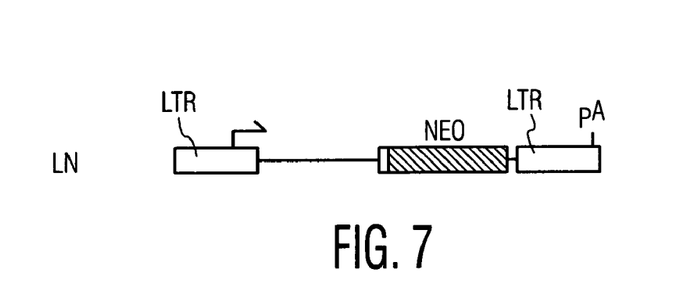
FIG. 7 is a map of the LN vector.

The LN vector (FIG. 7) (Miller, et al., *Biotechniques*, Vol. 7, No. 9, pgs. 980–990 (1989)), which includes a 5' LTR, a $neo^R$ gene, and a 3' LTR including a polyadenylation signal, was transduced into PA317 packaging cells according to the procedure of Miller, et al., 1989. PA317 packaging cells were plated at 5×10⁵ cells per 60 mm dish on day 1. On day 2, the culture medium was replaced with 4 ml fresh medium, and viral plasmid DNA from the LN vector was transfected onto the cells using the calcium phosphate precipitation procedure. (Corsaro, et al., *Somat. Cell Genet.*, Vol. 7, pgs. 603–616 (1981); Miller, et al., *Somatic Cell Mol. Genet.*, Vol. 12, pgs. 175–183 (1986)). For each plasmid sample, a DNA-$CaCl_2$ solution was made by mixing 25 μl of 2.0 M$CaCl_2$, 10 μg plasmid DNA (in 10 mM Tris-Cl, pH 7.5), and water to make 200 μl total. Precipitation buffer was prepared by mixing 100 μl 500 mM HEPES-NaOH (pH 7.1), 125 μl 2.0 M NaCl, 10 μl 150 mM $Na_2$ $HPO_4$—$NaH_2PO_4$ (pH 7.0), and water to make 1 ml total. DNA-$CaCl_2$ solution (200 μl) was added dropwise with constant agitation to 200 μl precipitation buffer. After 30 minutes at room temperature, the resultant fine precipitate was added to a dish of cells. The cells were exposed to the DNA precipitate until day 3 when the medium was aspirated and fresh medium was added. On day 4, the virus-containing medium was removed, centrifuged at 3,000×g for 5 minutes to remove cells and debris, and such recovered viruses may be used to infect cells. Through the above procedure, a viral titer of LN virus vector of 0.5–5×10⁶ cfu/ml is obtained.

D. Construction of LASN and Generation of Producer Cell Line Therefrom.

Figure 8:
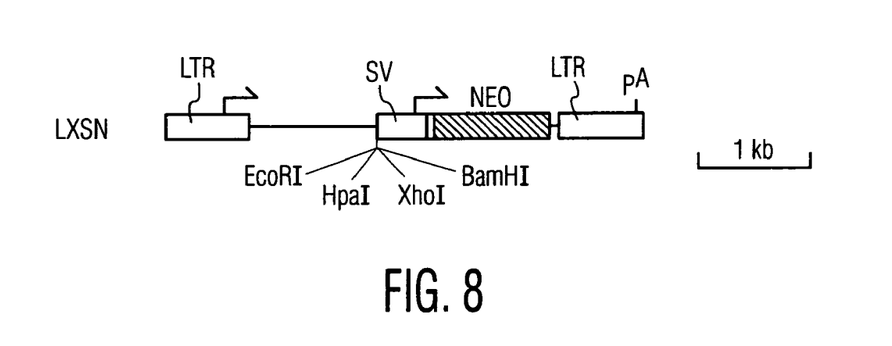
FIG. 8 is a map of the LXSN vector.
Figure 9:
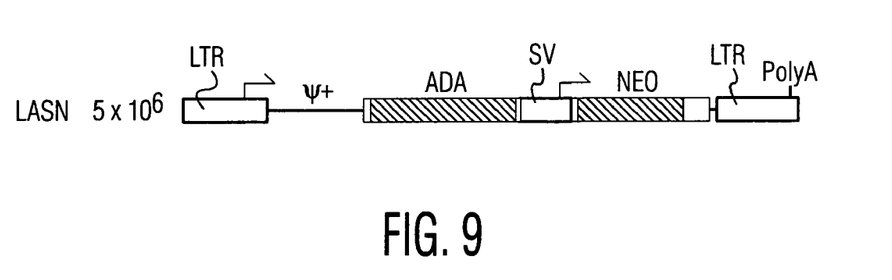
FIG. 9 is a map of the LASN vector.

LASN may be constructed as described in Hock, et al., Blood, Vol. 74, No. 2, pgs. 876–881, (Aug. 1, 1989). Alternatively, a PvuII to HindIII fragment from SV40 containing the SV40 early promoter (Fiers, et al., Nature, Vol. 273, pgs. 113–120 (1978); Reddy, et al., Science, Vol. 200, pgs. 494–502 (1978)), and a multiple cloning site including the EcoRI, HpaI, XhoI, and BamHI sites, was cloned into the LN vector (FIG. 7) to form the LXSN vector (FIG. 8) (Miller, et al., 1989)). ADA cDNA then was cloned into the LXSN vector to form the LASN vector. (FIG. 9) (Hock, et al., Blood, Vol. 74, No. 2, pgs. 876–881 (Aug. 1, 1989)). In the LASN vector, the ADA-encoding mRNA begins in the 5' retroviral LTR, continues through the ADA SV40, and $neo^R$ sequences, and terminates in the 3' LTR.

The LASN vector includes 4,700 base pairs. Base pairs 1–589 comprise the Moloney Murine Sarcoma Virus 5'LTR; base pairs 590–1462 comprise the packaging signal; base pairs 1463–2681 comprise the ADA cDNA with linkers; base pairs 1556–1558 comprise the ATG start codon for ADA; base pairs 2645–2647 comprise the TGA stop codon for ADA; base pairs 2682–3027 comprise the SV40 early promoter; base pairs 3028–4051 comprise the coding region of the $neo^R$ gene; base pairs 4052–4106 comrpise a polypurine (Poly A) site; and base pairs 4107–4700 comprise the Moloney Murine Leukemia Virus 3'LTR.

A producer cell line for generating LASN is generated as hereinabove mentioned with respect to the generation of LN vector particles. Through this procedure, a virus titer for LASN vector particles of 2–5×10⁵/ml is obtained.

Cell-free viral supernatants of LN viral vector, LASN viral vector, and GlNaSvAd viral vector were prepared in Dulbecco's Minimal Essential Medium (DMEM) with 10% fetal calf serum. E. Isolation and Culturing of Cord Blood Cells.

Umbilical cord blood samples were obtained from normal term deliveries by gravity drainage from the umbilical cord stump into CPD anticoagulant. Mononuclear cells were isolated by centrifugation on a two-step Ficoll/Hypaque-72% Percoll gradient, and by collecting and pooling the cells at both the plasma/Ficoll and the Ficoll/Percoll interfaces. In some of the experiments which follow, CD34+ cells were isolated using the Cell Pro CEPRATE system.

Cells were cultured at a final density of $0.5–1.0 \times 10^5$ cells/ml in 5% $CO_2$ at 37° C. The medium used was basal bone marrow medium (BBMM) consisting of IMDM with 30% fetal calf serum, 1% BSA (Sigma, St. Louis, Mo.), $10^{-6}$M hydrocortisone, 104M 2-mercaptoethanol, 2 mM L-glutamine, 50 U/ml penicillin, and 50 μg/ml streptomycin. In some of the following experiments, recombinant human growth factors were used at the following concentrations: Interleukin-3 at 10 μg/ml (Immunex Corp., Seattle, Wash.), Interleukin-6 at 50 U/ml (R+D Systems, Minneapolis, Minn.), and Mast Cell Growth Factor at 50 ng/ml (MGF, a c-kit ligand, Immunex.).

F. Transduction of Cord Blood Cells

For transductions, one volume of virus supernatant was added to one volume of cord blood cells in BBMM containing 2× growth factors, followed by addition of protamine to 5 μg/ml. The cells and virus were incubated overnight. For repeated transductions, cells were collected and resuspended in a fresh mixture of virus 1:1 with BBM and growth factors. After gene transfer, the cells were washed 3 times with Hank's buffered saline with FCS, counted, and plated in quadruplicate for colony-forming progenitor assays. G418 was added to two plates of each set at 10 mg/ml of active compound. After 14 to 16 days, colonies were counted as described in Nolta, et al., Human Gene Therapy, Vol. 1, pgs. 257–268 (1990).

In a first experiment, umbilical cord blood cells were exposed to LN vector supernatant (i) once; or (ii) daily for 3 days; or (iii) daily for three days while cultured with Interleukin-3, Interleukin-6, and MGF. The cells were evaluated for the presence of G418-resistant colonies. The results are shown in Table I below.

TABLE I

| Daily vector exposures | Medium | % G418-resistant colonies |
| --- | --- | --- |
| 1 | BBMM | 3.1 |
| 3 | BBMM | 9.8 |
| 3 | IL-3, IL-6, MGF | 30.4 |

As shown in Table I, three daily exposures to the vector supernatant increased the gene transfer threefold, while maximal gene transfer was obtained by using three exposures to the vector in the presence of Interleukin-3, Interleukin-6, and MGF.

In a second experiment, umbilical cord blood cells were exposed daily for 3 days to LN, LASN, or GlNaSvAd vector supernatant. The cells were cultured in (i) BBMM; (ii) BBMM plus Interleukin-3; (iii) BBMM plus Interleukin-3 and Interleukin-6; or (iv) BBMM plus Interleukin-3, Interleukin-6, and MGF. The cells were evaluated for G418-resistant colonies, and the results are shown in Table II below.

TABLE II

| | % G418-resistance | | |
| --- | --- | --- | --- |
| Growth Factors | LASN | Vector GlNaSvAd | LN |
| BBMM (control) | 3.2 | 5.6 | 4.8 |
| IL-3 | 15.2 | 15.7 | 13.6 |
| IL-3 plus IL-6 | 28.5 | 27.9 | 29.8 |
| IL-3, IL-6, and MGF | 32.1 | 30.6 | 28.6 |

The above results indicate that Interleukin-3 alone increased gene transfer, and the addition of Interleukin-6 to Interleukin-3 further increased gene transfer efficiency. Supplementation of Interleukin-3 and Interleukin-6 with MGF increased the transduction of cord blood progenitor cells slightly further.

Example 2

Umbilical cord blood, in amounts of from 60 to 200 ml, was collected after clamping of the umbilical cords of three newborn infants diagnosed prenatally as having ADA deficiency. 60 ml of blood were taken from Patient 1. This sample had a total of $5.2 \times 10^8$ cells, 0.72% of which, or $3.7 \times 10^6$, were CD34+ cells, as determined by FACS employing a fluorescent labeled CD34 antibody. 200 ml of blood were taken from Patient 2. This sample had a total of $22 \times 10^8$ cells, 0.83% of which, or $18 \times 10^6$, were CD34+ cells. 70 ml of blood were taken from Patient 3. This sample had a total of $8.6 \times 10^8$ cells, 0.9% of which, or $7.8 \times 10^6$, were CD34+ cells. All three cord blood samples were profoundly lymphopenic with no PHA-responsive T-cells, and had elevated levels of deoxyadenosine metabolites and decreased S-adenosyl homocysteine hydrolase (SAH) activity. Thus, there were multiple signs of ADA deficiency manifest at birth, despite the babies' circulatory proximity to the maternal systems which have at least heterozygote levels of ADA activity.

Mononuclear cells from the umbilical cord blood were isolated on a two-layer Percoll/Ficoll gradient. The cells then are incubated with biotinylated murine anti-CD34 antibody 12.8(CellPro, Bothell, Wash.) in PBS/1% bovine serum albumin (BSA) for 30 minutes at 4° C. at a concentration of $1 \times 10^8$ cells/ml. The cells were washed twice and adjusted to a concentration of $1 \times 10^8$ cells/ml in PBS/5% BSA. Antibody-treated cells then were passed over an avidin Biogel column (CellPro). Cells passing through the column were collected for analysis and the column was washed with PBS. CD34+ cells adhering to the column then were dislodged using mechanical agitation with a 10 ml pipette and collected in PBS/BSA.

The CD34+fraction obtained from the column was washed in PBS and counted. Aliquots were removed for FACS analysis and progenitor assays. $2.8 \times 10^6$ cells were obtained (post-column) from the blood sample of Patient 1, of which 32%, or $0.9 \times 10^6$, were CD34+ cells. $26.0 \times 10^6$ cells were obtained (post-column) from the blood sample of Patient 2, of which 62%, or $16.0 \times 10^6$, were CD34+ cells. $9.4 \times 10^6$ cells were obtained (post-column) from the blood sample of Patient 3, of which 47%, or $4.4 \times 10^6$, were CD34+ cells. The cells then were resuspended at a concentration of approximately $1 \times 10^5$/ml in LASN viral vector supernatant supplemented with 4 μg/ml protamine, 50 μg/ml Interleukin-6 (Sandoz, East Hanover, N.J.), 100 μg/ml stem cell factor (Amgen, Thousand Oaks, Calif.) and 20 μg/ml Interleukin-3 (Sandoz). The LASN viral supernatant was added daily for 3 days at a multiplicity of infection of about 6 vectors per cell. The cells were cultured in T25 tissue culture flasks (Costar) at 37° C. in a humidified incubator with 5% $CO_2$. At 24 and 48 hours of culture, complete media exchanges were done by collecting media and cells out of each flask, spinning down the cells and resuspending them at the same concentration in freshly-thawed retroviral supernatant with the above additives before transferring them back to the flask.

After a total of 64–72 hours in culture, the transduced cells were harvested from the flasks. Post-transduction, $3.7 \times 10^6$ cells were obtained from the cell culture of Patient 1. $62 \times 10^6$ cells were obtained from the cell culture of Patient 2, of which 63%, or $39 \times 10^6$, were $CD34^+$ cells as determined by FACS. $17 \times 10^6$ cells were obtained from the cell culture of Patient 3, of which 51%, or $8.7 \times 10^6$, were $CD34^+$ cells.

The harvested cells were washed twice and resuspended in normal saline. The cells then were infused into each infant intravenously in an amount of $1-10 \times 10^7$ cells/kg per infusion. One infusion was given to each infant. The total volume infused each day did not exceed 10 ml/kg body weight, and a test dose of 2–5% of the total volume was infused via peripheral vein followed by an observation period of 5–10 minutes. All three infants tolerated the infusions without apparent toxicities. The infants also were given PEG-ADA intramuscularly at a dosage of 30 units/kg twice weekly, and maintained in protective isolation.

In order to estimate the efficiency of the transduction of the vectors into the cells, $7 \times 10^3$ cells were taken from each of the cultures obtained from Patients 1, 2 and 3. The cells were cultured for two weeks, whereby $CD34^+$ cells differentiated into colony-forming units of granulocyte macrophages (CFU-GM). G418 resistance for each of these cultures then was determined. For Patient 1, 21.1% of the CFU-GM cells were G418 resistant. For Patient 2, 12.5% of the CFU-GM cells were G418 resistant. For Patient 3, 19.4% of the CFU-GM cells were G418 resistant.

The babies were discharged to home at approximately two months of age and are being followed as outpatients. Peripheral blood samples from each patient have been received on a 2–6 weekly schedule, both to monitor the status of their immune systems as standard clinical care, as well as to determine the efficacy of gene transfer.

Each of the babies has developed normal numbers of T lymphocytes, normal PHA responses, normalized levels of deoxyadenosine metabolites with normal growth and development to date. Each was given a tetanus immunization as part of the standard evaluation of the immune status of immune deficient infants. There are preliminary findings suggesting that they can now each produce a T lymphocyte blastogenic response to tetanus antigen in vitro, a sign indicating their development of antigen-specific immune function.

PCR analyses of peripheral blood samples shows that each child has circulating leukocytes which contain the vector-transferred ADA gene. Blood samples have been separated into a peripheral blood mononuclear (PBMC) cell fraction (lymphocytes and monocytes) and granulocyte fraction by ficoll-hypaque density centrifugation. Multiple aliquots of each cell fraction were frozen for subsequent DNA and RNA analyses. Initial samples obtained in the first 2–3 months did not show evidence of circulating PBMC with the gene above the limit of sensitivity (approximately 1 cell with the new ADA gene/100,000 cells). Granulocyte samples have been studied from one patient and did show gene-containing cells through this early period at about 1/10,000 cells. Subsequently, PBMC samples from all three patients have been showing the presence of gene containing cells, at levels ranging from 1/10,000 up to 1/1,000.

The above results indicate that there was effective gene transfer into at least some long-lived hematopoietic progenitor cells which are continuing to contribute to peripheral blood cell pools out to at least eight months.

All patents, publications, and database entries referenced in this specification are indicative of the level of skill of persons in the art to which the invention pertains. The disclosures of all such patents, publications (including published patent applications), and database entries are specifically incorporated herein by reference in their entirety to the same extent as if each such individual patent, publication, and database entry were specifically and individually indicated to be incorporated by reference.

It is to be understood, however, that the scope of the present invention is not to be limited to the specific embodiments described above. The invention may be practiced other than as particularly described and still be within the scope of the accompanying claims.

What is claimed is:

1. A method of expressing a therapeutic agent in a human, comprising:
   administering autologous CD34+ cells obtained from cord blood to said human, said autologous CD34+ cells having been genetically engineered to include at least one nucleic acid sequence encoding adenosine deaminase.

2. The method of claim 1 wherein said at least one nucleic acid sequence is contained in a viral vector.

3. The method of claim 2 wherein said viral vector is a retroviral vector.

4. The method of claim 1 wherein said CD34+ cells are administered in an amount of from about $5 \times 10^5$/kg to about $10 \times 10^7$/kg.

5. A method of treating a human patient suffering from severe combined immune deficiency resulting from adenosine deaminase deficiency, comprising:
   administering autologous CD34+ cells obtained from cord blood to said patient, said autologous CD34+ cells having been genetically engineered to include a nucleic acid sequence encoding adenosine deaminase, said autologous CD34+ cells being administered to said patient in an amount effective to treat said severe combined immune deficiency resulting from adenosine deaminase deficiency in said patient by providing said patient with an effective amount of said adenosine deaminase by expression of said nucleic acid sequence encoding adenosine deaminase in said patient.

6. The method of claim 5 wherein said nucleic acid sequence encoding adenosine deaminase is contained in a viral vector.

7. The method of claim 6 wherein said viral vector is a retroviral vector.

8. The method of claim 5 wherein said CD34+ cells are administered in an amount of from about $5 \times 10^5$/kg to about $10 \times 10^7$/kg.

9. The method of claim 5 wherein said patient is a newborn infant and said CD34+ cells are obtained from the cord blood of said newborn infant.

10. A method of treating an infant suffering from severe combined immune deficiency resulting from adenosine deaminase deficiency, comprising:
    obtaining cord blood from said infant;
    separating CD34+ cells from said cord blood;
    cultivating said CD34+ cells obtained from said cord blood in the presence of (i) Interleukin-3; (ii) Interleukin-6; and (iii) a c-kit ligand;
    transfecting said CD34+ cells with a nucleic acid sequence encoding adenosine deaminase; and
    administering to said infant said transfected CD34+ cells, said CD34+ cells being administered to said infant in an amount effective to treat severe combined immune deficiency resulting from adenosine deaminase deficiency in said infant by providing said infant with an effective amount of said adenosine deaminase by expression of said nucleic acid sequence encoding adenosine deaminase in said infant.

11. The method of claim 10 wherein said nucleic acid sequence encoding adenosine deaminase is contained in a viral vector.

12. The method of claim 11 wherein said viral vector is a retroviral vector.

13. The method of claim 10 wherein said CD34+ cells are administered in an amount of from about $5 \times 10^5$/kg to about $10 \times 10^7$/kg.

14. The method of claim 10 wherein said patient is a newborn infant and said CD34+ cells are obtained from the cord blood of said newborn infant.

15. The method of claim 4 wherein said CD34+ cells are administered in an amount of from about $5 \times 10^5$/kg to about $1 \times 10^7$/kg.

16. The method of claim 15 wherein said CD34+ cells are administered in an amount of from about $5 \times 10^5$/kg to about $5 \times 10^6$/kg.

* * * * *

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 51 bases
      (B) TYPE: nucleic acid
      (C) STRANDEDNESS: double
      (D) TOPOLOGY: linear    (ii) MOLECULE TYPE: plasmid DNA    (ix) FEATURE:
      (A) NAME/KEY: multiple cloning site (xi) SEQUENCE DESCRIPTION: SEQ ID NO: 1:

AATTCGCGGC CGCTACGTAG TCGACGGATC CCTCGAGAAG CTTGGGCCCA T        51